US012582346B2

(12) United States Patent
Karjalainen et al.

(10) Patent No.: US 12,582,346 B2
(45) Date of Patent: **\*Mar. 24, 2026**

(54) MEASUREMENT UNIT AND MONITORING SYSTEM FOR MONITORING INDICATOR OF PARKINSON'S DISEASE IN PERSON

(71) Applicant: ADAMANT HEALTH OY, Helsinki (FI)

(72) Inventors: Pasi Karjalainen, Kuopio (FI); Saara Rissanen, Kuopio (FI); Verneri Ruonala, Helsinki (FI)

(73) Assignee: Adamant Health Oy, Helsinki (FI)

( \* ) Notice: Subject to any disclaimer, the term of this patent is extended or adjusted under 35 U.S.C. 154(b) by 752 days.

This patent is subject to a terminal disclaimer.

(21) Appl. No.: 17/434,547

(22) PCT Filed: Feb. 28, 2019

(86) PCT No.: PCT/FI2019/050163
§ 371 (c)(1),
(2) Date: Aug. 27, 2021

(87) PCT Pub. No.: WO2020/174122
PCT Pub. Date: Sep. 3, 2020

(65) Prior Publication Data
US 2022/0133211 A1    May 5, 2022

(51) Int. Cl.
*A61B 5/389*        (2021.01)
*A61B 5/00*        (2006.01)
*A61B 5/11*        (2006.01)
(52) U.S. Cl.
CPC .......... *A61B 5/4082* (2013.01); *A61B 5/0022* (2013.01); *A61B 5/1114* (2013.01);
(Continued)

(58) Field of Classification Search
CPC ... A61B 5/4082; A61B 5/0022; A61B 5/1114; A61B 5/389; A61B 5/4842; A61B 5/742;
(Continued)

(56) References Cited

U.S. PATENT DOCUMENTS 5,511,421 A *   4/1996   Kudo .................... G01P 15/124
                                                73/514.01
6,511,442 B1 *  1/2003   Lathan ..................... A61B 5/16
                                                600/595

(Continued)

FOREIGN PATENT DOCUMENTS

WO    WO-2014176420 A1 *  10/2014   ............. A61B 5/004

OTHER PUBLICATIONS

Rissanen, et.al., Surface EMG and acceleration signals in Parkinson's disease: feature extraction and cluster analysis, Jul. 17, 2008, International Federation for Medical and Biological Engineering, pp. 849-858 (Year: 2008).*

(Continued)

*Primary Examiner* — Adam J Eiseman
(74) *Attorney, Agent, or Firm* — Ziegler IP Law Group, LLC.

(57)        ABSTRACT

The present disclosure describes a measurement unit including measurement electronics, a wireless transceiver unit, and a processing. The measurement electronics are configured to measure an EMG signal and a motion signal from a limb of a person. The processing unit is configured to determine a principal component representation of the EMG signal and the motion signal in real time, wherein the principal component representation represents a projection of at least one feature of the EMG signal and at least one feature of the motion signal into at least one uncorrelated feature in a feature space formed by orthogonal basis vectors, and trans- (Continued)

mit the principal component representation to an external system with the wireless transceiver unit.

8 Claims, 6 Drawing Sheets

(52) U.S. Cl.
CPC ............ *A61B 5/389* (2021.01); *A61B 5/4842* (2013.01); *A61B 5/742* (2013.01); *A61B 2562/0219* (2013.01)

(58) Field of Classification Search
CPC . A61B 2562/0219; A61B 5/7264; A61B 5/40; A61B 5/296; A61B 5/397; A61B 5/6833; A61B 2562/16–166; A61B 5/7235; A61B 2560/04; A61B 5/11–1101; A61B 2562/0209; A61B 5/313; G05B 2219/34017; G06F 15/8053; G06E 1/045; G06E 3/008; A61H 2230/60
See application file for complete search history.

(56) References Cited

U.S. PATENT DOCUMENTS

| 8,187,209 | B1 * | 5/2012 | Giuffrida | A61M 5/1723 |
| | | | | 600/595 |
| 9,314,190 | B1 | 4/2016 | Giuffrida et al. | |
| 2005/0240086 | A1 * | 10/2005 | Akay | A61B 5/1124 |
| | | | | 600/595 |
| 2006/0065054 | A1 * | 3/2006 | Ikeda | G01P 15/0802 |
| | | | | 73/514.33 |
| 2008/0223132 | A1 * | 9/2008 | Terada | G01P 15/09 |
| | | | | 73/514.34 |
| 2010/0106044 | A1 | 4/2010 | Linderman | |
| 2012/0172745 | A1 | 7/2012 | Miyazaki et al. | |
| 2013/0317648 | A1 * | 11/2013 | Assad | G06F 3/011 |
| | | | | 700/258 |
| 2016/0345817 | A1 * | 12/2016 | Calderon | A61B 17/435 |
| 2017/0164901 | A1 * | 6/2017 | Shusterman | A61B 5/0024 |

OTHER PUBLICATIONS

V. Ruonala, A. Meigal, S. M. Rissanen, O. Airaksinen, M. Kankaanpää and P. A. Karjalainen, "EMG signal morphology in essential tremor and Parkinson's disease," 2013 35th Annual International Conference of the IEEE Engineering in Medicine and Biology Society (EMBC), Osaka, Japan, 2013, pp. 5765-5768, doi: 10.1109/E.*
Andreas Daffertshofer, et al., "PCA in studying coordination and variability: a tutorial", Clinical Biomechanics, vol. 19, No. 4, May 1, 2004, pp. 415-428 (14 pages).
X. He, et al., "A novel experimental method to evaluate motor task control in Parkinson's patients", 35th Annual International Conference of the IEEE EMBS, Jul. 3, 2013, pp. 6587-6590 (4 pages).
Donatas Lukšys, et al., "Differentiation of Gait Using Principal Component Analysis and Application for Parkinson's Disease Monitoring", International Conference BIOMDLORE, Jun. 28, 2018, 4 pages.
"ME6000 Biomonitor", Device Manual, Mega Electronics Ltd., 2004, 44 pages, http://www.meditech.nu/files/2017-02/1486987227_me6000.pdf.
Saara M. Rissanen, et al., "Analysis of Dynamic Voluntary Muscle Contractions in Parkinson's Disease", IEEE Transactions on Biomedical Engineering, vol. 56, No. 9, Sep. 1, 2009, pp. 2280-2288 (9 pages).p.
International Search Report for PCT/FI2019/050163 dated Oct. 4, 2019, 6 pages.
Written Opinion of the ISA for PCT/FI2019/050163 dated Oct. 4, 2019, 7 pages.
Hiermens et al., "European Recommendations for Surface ElectroMyoGraphy: Results of the SENIAM project", Roessingh Research and Development, ISBN 90-75452-15-2, 1999, Preface and Contents, 4 total pages.

* cited by examiner

MEASUREMENT UNIT AND MONITORING SYSTEM FOR MONITORING INDICATOR OF PARKINSON'S DISEASE IN PERSON

BACKGROUND OF THE INVENTION

Field of the Invention

The invention relates to measurement and analysis of biosignals, and in particular, to a system for monitoring at least one indicator of Parkinson's disease (PD) in biosignals measured from a person.

Description of the Related Art

Parkinson's disease (PD) is a long-term degenerative disorder of the central nervous system that mainly affects the motor system. The symptoms generally come on slowly over time. As the disease progresses, the symptoms become more and more unpredictable. At present, there is no accurate data analysis about the symptoms. It is difficult to form a comprehensive view of the time varying symptoms and to find a correct drug and its dosage, and the scheduling of doses, particular in cases where the disease has already progressed to later stages. It may also be difficult to adjust deep brain stimulation (DBS) settings, and to choose optimal treatment method in each situation.

SUMMARY OF THE INVENTION

An object of the present disclosure is to provide a monitoring system and a measurement unit so as to alleviate the above disadvantages. The object of the disclosure is achieved by a monitoring system and a measurement unit as disclosed and claimed.

A monitoring system and a measurement unit according to the present disclosure may be used to monitor different indicators of PD in the measurement data. A principal component representation may be formed based on the EMG and motion data. Principal components of the principal component representation may be selected such that the principal component representation groups the measurement data into meaningful categories representing different indicators of type and/or stage and/or severity of symptoms or treatment response of PD. Values of the different indicators of PD in the measurement data can be calculated, and an assessment of the condition of the person can be formed on the basis of these values.

A monitoring system and a measurement unit according to the present disclosure provide a reliable, computationally cost-efficient tool for providing information that can be used in monitoring indicators of PD in a person, in assessing progress of PD in the person, and in determining the efficiency of a treatment/medication for PD in the person. Most of the functionalities of the monitoring system can be performed on the measurement unit in real time. As a result, the amount of data to be sent for further analysis can be kept at a very low level. This enables the use of low-power, long range wireless communication technologies.

The monitoring system and measurement unit allow the person to move freely during a measurement period. Thus, the monitoring system and measurement unit enable measurement periods that may last several days instead of minutes or few hours. The ability to monitor and analyse continuous measurement data over longer periods of time can have a significant effect on forming a clear view on the symptoms and planning of optimal therapy with regards to drug type, and its dosage, and the dosage scheduling. Continuous and longer monitoring of data may also help in adjusting deep brain stimulation settings, and choosing optimal treatment method in each situation.

BRIEF DESCRIPTION OF THE DRAWINGS

In the following the invention will be described in greater detail by means of preferred embodiments with reference to the attached drawings, in which.

DESCRIPTION OF THE PREFERRED EMBODIMENTS

Figure 1:
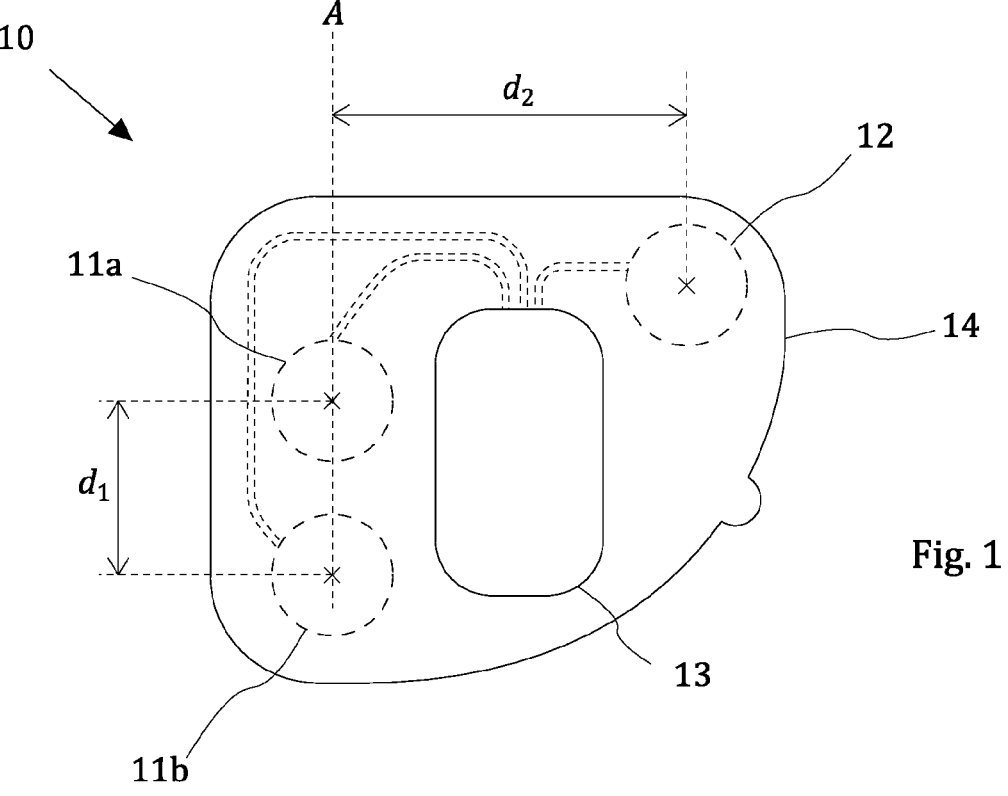
FIG. 1 shows an example of an electrode patch that can be used with a monitoring system according to the present disclosure.

The present disclosure describes a measurement unit and a monitoring system for monitoring an indicator of PD in a person. In the context of the present disclosure, the term "indicator of PD" refers to a value calculated based on biosignal data, such as EMG and motion signal data, of the person. In the context of the present disclosure, biosignal data may represent samples of a biosignal or biosignals measured from the person, for example. The indicator may be utilized by medical personnel in making decisions on a diagnosis and/or treatment of the person's condition.

A monitoring system according to the present disclosure may be configured to receive an EMG signal originating from an upper or lower limb of the person and a motion signal associated with the EMG signal, determine a principal component representation of features of the person's measured biosignal data, and determine a value of at least one indicator of PD based on the principal component representation. The condition of the person may then be interpreted on the basis of the determined value of the at least one indicator.

In the context of the present disclosure, the principal component representation represents a projection of original signal features that may have correlations between each other into uncorrelated signal features in a new feature space formed by orthogonal basis vectors. The principal component representation may be based on at least one feature of the EMG signal and the motion signal, for example. Preferably, the principal component representation may be based on at least one feature of the EMG signal and at least one feature of an acceleration signal representing the motion signal. The at least one feature of the EMG signal and the at least one feature of the acceleration signal preferably comprise at least a) sample kurtosis or crossing rate variable, b) recurrence rate of the EMG signal, and c) sample entropy of the acceleration signal.

Various features of the biosignal data (i.e. samples of the EMG signal and the motion signal) may be utilized in determining the value of the at least one indicator of PD. These features include statistical features of the signals, such as sample histograms, kurtosis and crossing rate, and spectral-based features, such as Fourier transform, periodogram and wavelets. Further, said features may include parameters based on nonlinear dynamics and interrelation between the EMG and the motion data, such as coherence and different types of cross-entropies.

Features extracted from the biosignal data form a feature vector. In order to eliminate possible correlations between the extracted features in the feature vector, the feature vector may be modelled as a weighted sum of basis vectors, where the basis vectors may have been previously solved as eigenvectors of a sample correlation matrix that represents correlations between the extracted features. In other words, the feature vector is projected onto the new feature space formed by the basis vectors. Principal components representing weights for the weighted sum may be solved for the feature vector as a least squares solution, for example. The principal components are new, uncorrelated features that represent the measurement data in a new space formed by the basis vectors. Together, the principal components form a principal component representation.

In order to reduce complexity of the data, only the most significant principal components may be selected, and an approximation of the measurement data in a reduced-dimension feature space. For example, the principal components may be selected such that measurement data from persons with PD (or a specific type of PD) cluster together in the reduced-dimension feature space. Further, the principal components may also be selected such that the data forms clusters representing different severity/stage of PD or effectiveness of particular treatments, for example. Based on the clusters, simple rules for categorizing measurement results can be formed. Once the rules have been determined, measurement can be reliably categorized by applying the rules to a principal component representation of the EMG and motion data.

A monitoring system according to the present disclosure may be implemented in various ways. For example, a measurement arrangement implementing the monitoring system may comprise a flexible or rigid electrode patch a, (wearable) measurement unit connected to the electrodes of the electrode patch, and an external system acting as an analysis unit. Some (or even most) of the features of the monitoring system may be implemented on the measurement unit.

A measurement unit according to the present disclosure may comprise measurement electronics for measuring an EMG signal and a motion signal from the limb of the person, and a wireless transceiver unit for transmitting and receiving data wirelessly to the external system. Wireless communication enables the person move more freely during the measurements. The measurement electronics may comprise electronic circuitry configured to measure an EMG signal originating from electrodes which may be in the form of an electrode patch, for example. The electronic circuitry may comprise an A/D converter and a (analog and/or digital) filter, for example.

In addition, the measurement electronics may comprise electronic circuitry dedicated for measuring the motion signal. In the context of the present disclosure, the term "motion signal" refers to a signal that carries a sufficient amount of information on the movement of the limb of the person in order to be able to monitor PD-related signal features in the movement of the limb. The motion signal data may represent samples of measurements measuring motion of a limb of a person. The motion signal may represent motion in one or more directions (e.g. x-, y-, and z-direction). The motion data may originate from a motion sensor attached to the limb of the person, for example. In some embodiments, the motion sensor may be a 3D-motion sensor, for example. The type and configuration (sample rate, operating range) of the motion sensor may be selected for measuring motion data associated muscle activity, and in particular with PD, e.g. tremors. Thus, sample rate of the measured biosignals is preferably at least 30 Hz. In some embodiments, the sensor or sensors for measuring the motion of the limb may be integrated to the measurement unit. For example, the measurement unit may comprise an acceleration sensor, a gyroscope, or even a complete IMU (inertial measurement unit). Alternatively, the motion signal may originate from an external motion sensor in communication with the measurement unit.

It may be desirable to try to minimize the amount of data transmitted by the measurement unit. The measurement unit may be configured to perform some of the functionalities of the monitoring system according to the present disclosure. In order to achieve this, the measurement unit may further comprise a processing unit. The processing unit may be configured to determine a principal component representation in real time, and transmit the principal component representation to an external system with the wireless transceiver unit. As discussed above, the principal component representation may represent a projection of at least one feature of the EMG signal and the motion signal into uncorrelated features in a feature space formed by orthogonal basis vectors. The processing unit may be a processor, a DSP, an FPGA, and/or an ASIC coupled with memory, for example.

Once the principal component representation has been determined, it can be sent to the external system for further analysis. In this manner, the amount of data to be sent to the external system can be significantly reduced. With a measurement unit according to the present disclosure, a principal component representation of the measurements may be sent only a few times per second. For example, the measurement unit may send the principal component representation at a rate of less than 10 times per second, or even less than 2 times per second.

The low data transfer capability requirements enable the use of low-power wireless communication. For example, the wireless transceiver may be a low-power, long-range transceiver, such as a transceiver based on LoRa (Long Range) technology. By using a low-power communication technology, the operating time of the portable measurement unit can be extended. Further, the use of the low-power communications enables the use of the monitoring system even if a high-speed wireless data transfer is not available.

In order to determine the principal component representation locally on the measurement unit, the processing unit may be configured to extract the at least one feature of the EMG signal and at least one feature of the motion signal, form a feature vector on the basis of the at least one extracted feature, model the feature vector as a weighted sum of basis vectors, where the basis vectors are eigenvectors of a sample correlation matrix, solve the weights of for the weighted sum, and use the solved weights as principal components of the principal component representation.

In order to facilitate calculation of the principal component representation in real time on the measurement unit, time-recursive calculation may be used. The sample correlation matrix may be updated on the basis of the feature vector. This may occur at predetermined intervals, for example. Forming new values of the sample correlation matrix may be performed on the basis of values of the extracted features and previous values of the sample correlation matrix. An initial sample correlation matrix may have been formed on the basis of measurement data from a plurality of persons, for example.

As mentioned above, the monitoring system may further comprise an external system. The external system may be in the form of an analysis unit configured to receive the principal component representation originating from the measurement unit and determine an indicator of PD based on the principal component representation. The analysis unit may be configured to perform further analysis on the principal component representation and/or to present the principal component representation on a display, for example. A computer, cluster of computer servers, or a computing cloud may be used to implement the analysis unit of a monitoring system according to the present disclosure. The analysis unit may receive the principal component representation directly from the measurement unit or the principal component representation may be relayed via transceiver unit. The transceiver unit may be a wireless communications unit, such as a wireless internet router, for example. A smart phone, tablet computer or other portable computing device with wireless communications capabilities may also be used as a transceiver unit.

In the following the above-described aspects are discussed in more detail in view of examples.

Figure 3:
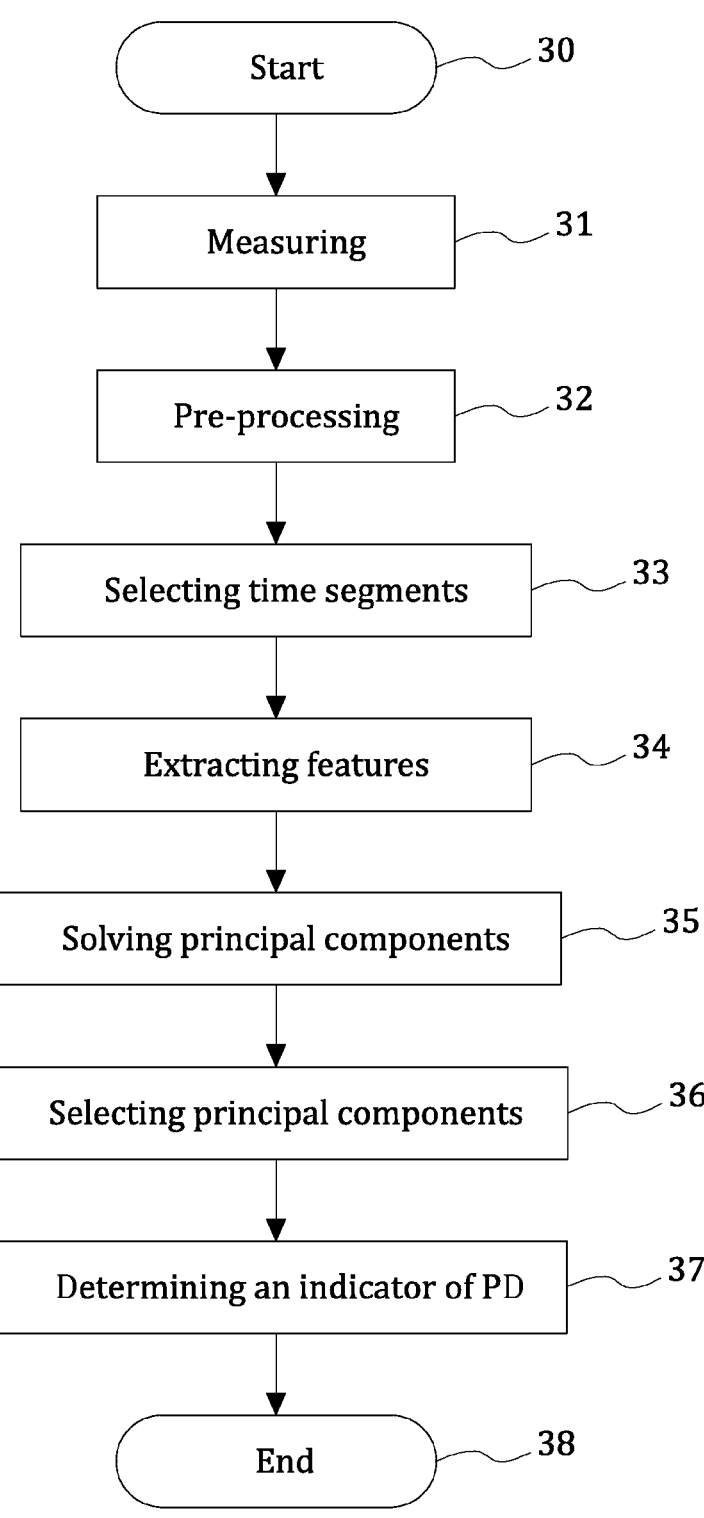
FIG. 3 shows an exemplary, simplified flow diagram of determining indicators of PD.

FIG. 3 shows an exemplary, simplified flow diagram of operation of a monitoring system according to the present disclosure. In FIG. 3, the flow diagram comprises an initial step 30, follows through consecutive steps 31-37, and finally ends at end step 38.

The procedure starts at step 30 from which the procedure continues to step 31. In step 31, raw EMG signals are band-pass filtered, amplified and A/D converted. The band-pass filter may be an analog anti-aliasing filter (Butterworth, band-pass 1-500 Hz), and the A/D conversion may be made with a 14-bit A/D converter, for example. Further, motion of limb is registered by using an accelerometer, e.g. a tri-axial accelerometer (range ±16 g, 14-bit A/D converter).

Next, in step 32, EMG- and motion signals are preprocessed. Possible noise may be removed from measured EMG data by using low-pass or band-pass and/or notch filtering, for example. The noise may be originated from surrounding electrical devices (e.g. a DBS unit) and motion, for example.

In the subsequent step 33, representative time segments of data are selected for analysis. Preferably, these segments include muscle activities measured during static and dynamic contractions. In addition, these segments preferably cover different times of day (morning, afternoon, evening and night).

Next, in step 34, several features are extracted from the EMG and motion signals. These features may include at least a sample histogram, parameters describing EMG morphology (e.g. sample kurtosis and crossing rate variable) and parameters based on nonlinear dynamics (e.g. recurrence rate of the EMG signal and sample entropy of an acceleration signal used as the motion signal), for example.

In the subsequent step 35, extracted EMG and motion signal features are used to form a feature vector. The feature vector may then be modelled as a weighted sum of basis vectors, where the basis vectors may have been previously solved as eigenvectors of a sample correlation matrix. The correlation matrix is calculated based on the feature vector, and it represents correlations between the extracted features. By modelling the feature vector as a weighted sum of the basis vectors, the original feature vector is projected into a new feature vector on the space formed by the basis vectors. Since the basis vectors are orthogonal, the features in the new feature vector are uncorrelated with respect to each other. The weights of the new feature vector may be solved as a least squares solution, for example.

The sample correlation matrix may be updated in a time-recursive manner. For example, a sample correlation matrix R may be updated as follows:

$$R_n = (1-\alpha)R_{n-1} + \alpha X X^T \qquad (1)$$

where $R_n$ represents the new sample correlation matrix R, $R_{n-1}$ represents the previous sample correlation matrix, coefficient a is a scalar (real number $0<a<1$), X is a column vector of features and $X^T$ is its transpose. Coefficient $\alpha$ may be used to adjust the adaptation of the algorithm and its initial value is adjusted in the beginning of the measurement session. For a homogenous patient group, coefficient $\alpha$ may be a constant.

An initial sample correlation matrix may be formed on the basis of gathered person data, for example, or the initial matrix may be formed on the basis of measurement data from a plurality of persons. A set of feature vectors may be formed using preliminary data, and the initial sample correlation matrix can be formed based on these feature vectors.

The solved principal components may be used to identify changes in the neuromuscular and motor function of subjects between different times of day, between different DBS settings, or between different treatment methods, for example. However, in order to reduce the complexity of the data, only the most significant principal components with regards to symptom severity, treatment response and type of PD may be chosen for further analysis. In step 36, a set of principal components is selected. This set forms a new, reduced-dimension feature vector that may be sent to an external system for the further analysis.

Next, in step 37, the chosen principal components may be used for calculation of indicator that presents the clinical condition of person. Step 37 may be performed on the external system. The calculated indicator may be a time-varying scalar value and it may be presented on a display as a graph, for example. The indicator may also be of higher dimension such as a point in two-dimensional plane, for example.

The procedure then ends at step 38.

Figure 5:
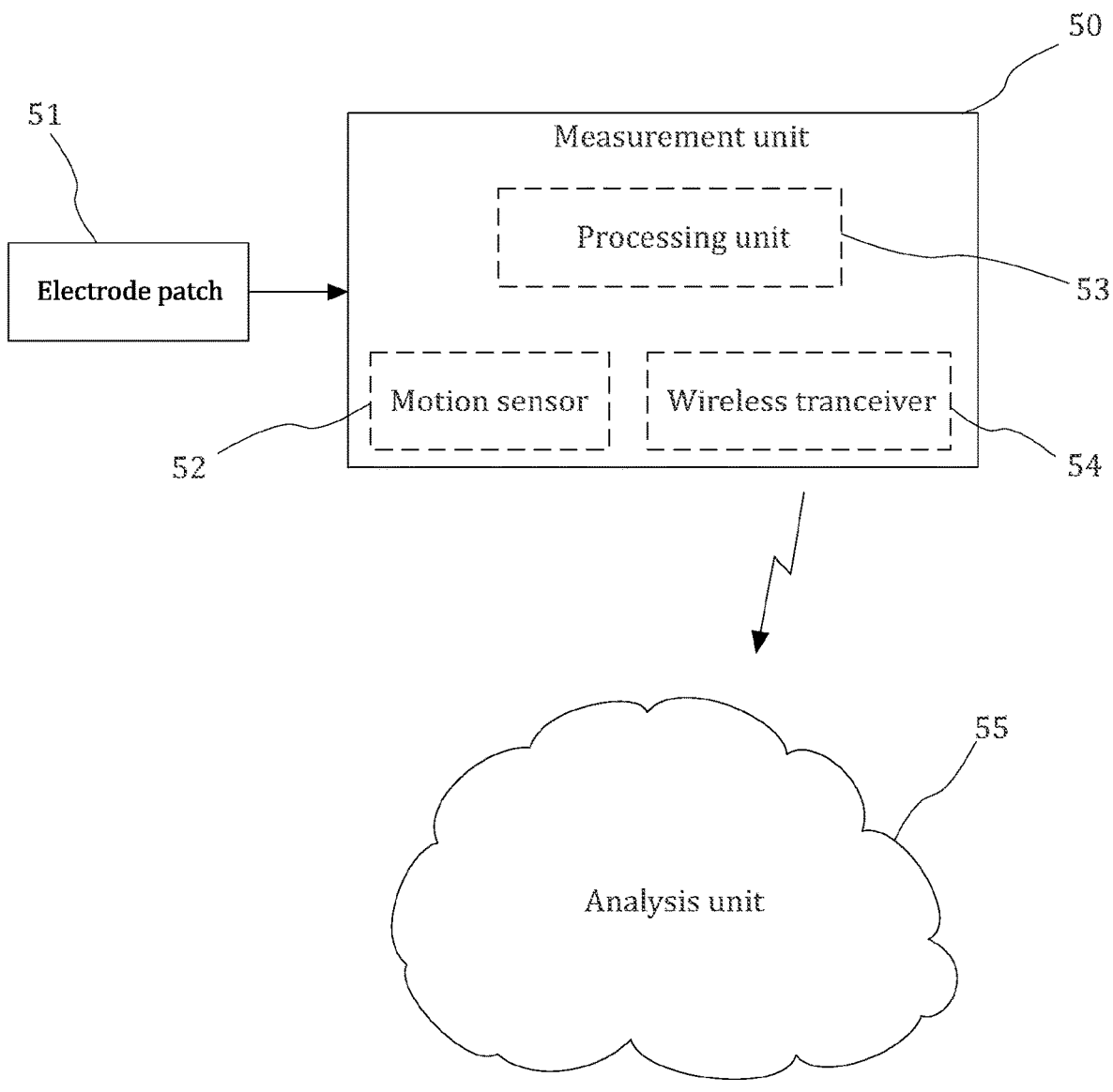
FIG. 5 shows an example of a measurement arrangement utilizing a measurement unit according to the present disclosure.

Some aspects of implementing a monitoring system according to the present disclosure are next discussed in more detail. As mentioned above, some or even most of the features of a monitoring system according to the present disclosure (e.g. a monitoring system as described in the example of FIG. 3) may be implemented on a measurement unit according to the present disclosure. FIG. 5 shows an example of a measurement arrangement implementing a monitoring system according to the present disclosure while utilizing a measurement unit 50 according to the present disclosure. In FIG. 5, electrical activation of a muscle is registered in the form of an EMG signal by using an electrode patch 51. The measurement unit 50 comprises measurement electronics for measuring the EMG signals from electrodes of the electrode patch 51. Alternatively, the measurement electronics may be integrated on the electrode patch 51 and the electrode patch 51 may send a measured EMG signal to the measurement unit 50.

In addition, limb motion is simultaneously registered by using a motion sensor 52. In FIG. 5, the motion sensor 52 is an accelerometer integrated to the measurement unit 50. Alternatively, the motion sensor may be a separate unit.

Further, the measurement unit 50 comprises a processing unit 53. The processing unit 53 may be a processor, a DSP, an FPGA, and/or an ASIC coupled with memory, for example. The electrode patch 50 and the motion sensor 51 provide an EMG signal and an acceleration signal (e.g. in the form of analog voltage signals) to the processing unit 53. The processing unit 53 may be configured to determine a principal component representation of the EMG signal and the motion signal, and transmit the principal component representation to be received by an external system 55.

As discussed earlier, the principal component representation represents a projection of at least one feature of the EMG signal and the motion signal into a feature space formed by orthogonal basis vectors. In FIG. 5, the measurement unit 50 comprises a wireless transceiver unit 54 that the measurement unit 50 uses to send the principal component representation (a reduced-dimension vector) to be received by an external system 55 acting as an analysis unit. The transceiver unit 54 may implement a low-power communications technology, such as LoRa technology. The transceiver unit may communicate directly with the external system 55, or it may send the principal component representation to the external system 55 via a router device, for example. The router device may be a wireless communications unit, such as a wireless internet router having LoRa capabilities, for example.

In FIG. 5, the principal component representation is sent to an analysis unit 55 that may be a computer, server or a cloud-computing system containing an analysis program, for example. The analysis program may be configured for monitoring an indicator of PD in the person. The analysis program may be configured to determine a value of the indicator of PD based on the principal component representation. For example, the analysis program may implement the step 37 of the example of FIG. 3 in order to detect an indicator of Parkinson's disease. Once the analysis program has been executed, the analysis results may be sent to a cloud-based database, from where they can be accessed by the doctor who is either in charge of the person's treatment or asked to give his/her statement on results, for example. Alternatively, or in addition, the analysis unit 55 may comprise a display and the analysis may be configured to show the principal component representation as a visual representation on the display.

Figure 6:
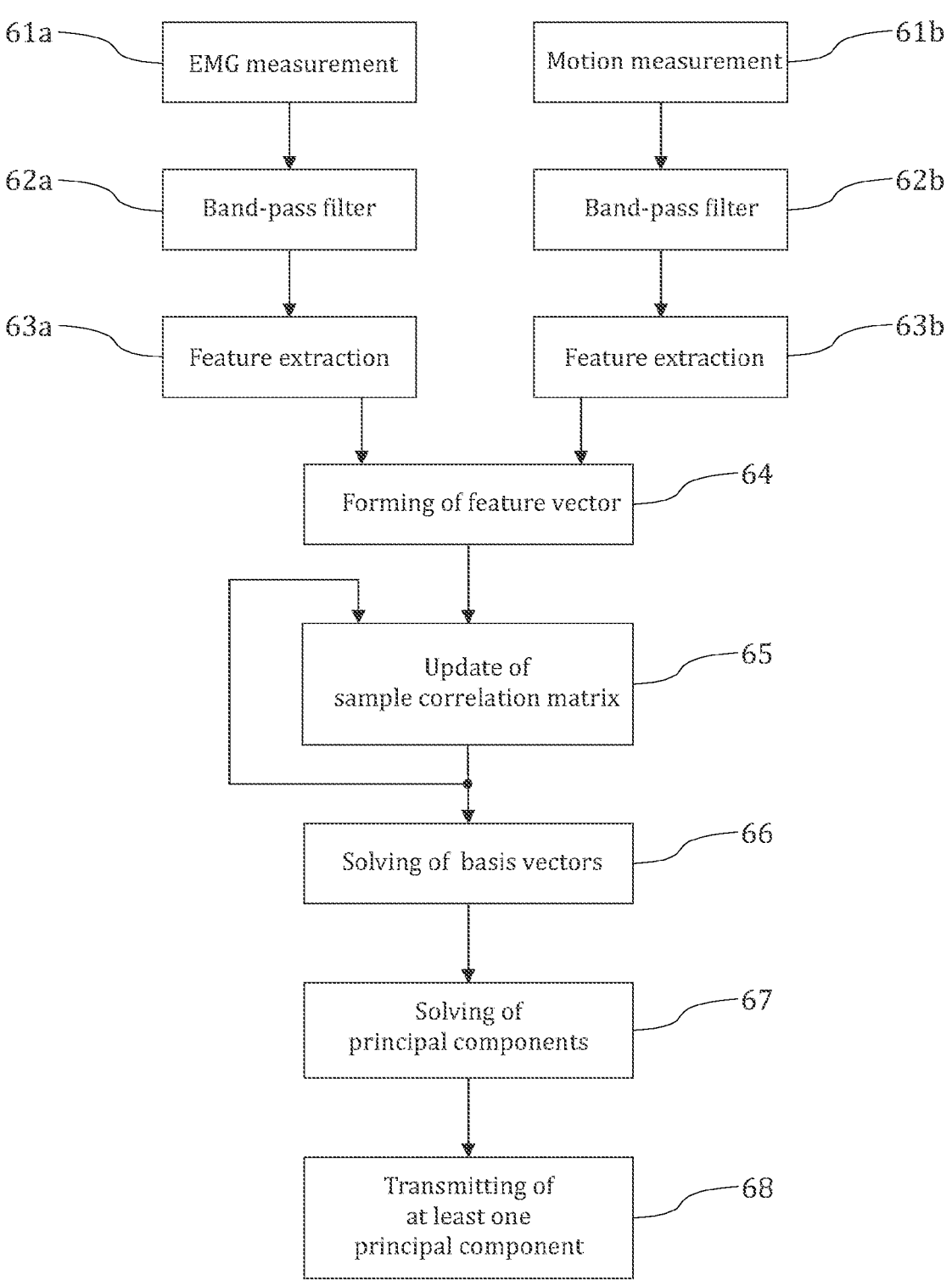
FIG. 6 shows an exemplary block diagram of calculation of principal component representation on a measurement unit according to the present disclosure.

Next, aspects of a measurement unit according to the present disclosure are discussed in more detail in view of an example. FIG. 6 shows an exemplary block diagram of features of the monitoring system implemented on a measurement unit according to the present disclosure. The measurement unit may be similar or the same as in FIG. 5. In FIG. 6, blocks 61*a* to 63*a* relate to measurement, preprocessing and feature extraction of an EMG signal. Blocks 61*b* to 63*b* correspondingly relate to measurement, preprocessing and feature extraction of a motion signal. Blocks 64 to 68 relate to calculation and transmitting of principal components based on the extracted features.

In block 61*a*, an EMG signal is measured. The EMG signal may be registered at a sampling frequency of at least 1 kHz, for example. A signal segment having a length of 250-2000 ms, for example, may then be chosen and filtered with a band-pass filter, as shown in block 62*a*. The passband of the filter may be 10 Hz to 500 Hz, for example. In block 63*a*, features are then extracted from the filtered signal. These features may include sample kurtosis and recurrence rate of the EMG signal, for example. If the filtered signal contains artefacts (such as powerline noise, stimulation artefacts, or ECG artefacts), these artefacts may be removed before the feature extraction.

Similarly, a motion signal is measured in 61*b*. The motion signal may be registered at a sampling frequency of at least 30 Hz, for example. A signal segment having a length of 250-2000 ms, for example, may then be chosen and filtered with a band-pass filter, as shown in block 62*b*. The passband of the filter may be 3 to 15 Hz, for example. In block 63*b*, features are then extracted from the filtered signal. These features may include sample entropy and signal power of the motion signal, for example. If the motion signal is multidimensional, a resultant of the motion signal may be calculated before filtering, and the resultant may instead be band-pass filtered in block 63*b*.

In block 64, a feature vector is formed based on the features extracted by feature-extraction blocks 63*a* and 63*b*. The feature vector is then used to update the sample correlation matrix in block 65. The updated value of the sample correlation matrix is calculated on the basis of the feature vector and the preceding value of the sample correlation matrix. An initial value may be set for the sample correlation matrix based on preliminary measurement data in order to produce a good starting point for the iterative nature of the update process.

The eigenvectors of the sample correlation matrix are then calculated in block 66. These eigenvectors are used as basis vectors for a new feature space. In block 67, the feature vector determined in block 64 is projected onto the new feature space, and the weights of the projection are used as the principal components. In block 68, at least one of the principal components is sent to an external system for further analysis.

Figure 7:
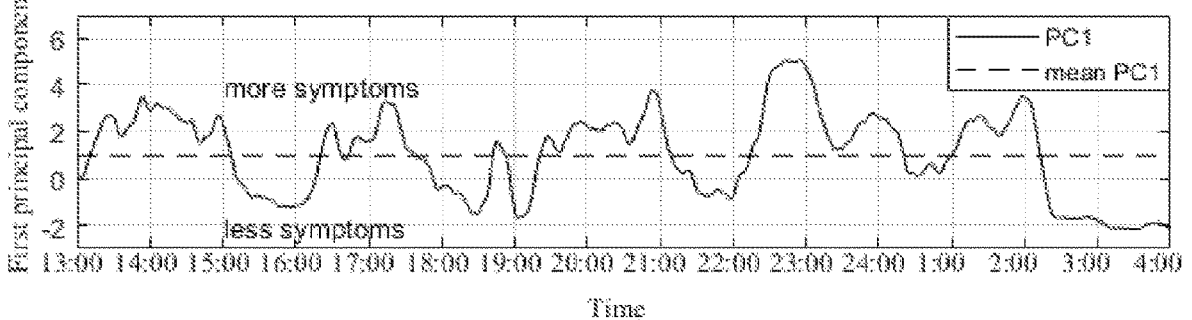
FIG. 7 shows an exemplary graph of a principal component plotted as a curve.

Next, aspects of possible uses of a monitoring system according to the present disclosure are discussed in more detail. The above-discussed monitoring system may be used as follows, for example. First, the skin of the person over a muscle of interest is preferably shaved (if required) and rubbed with alcohol. An electrode patch may then be placed on the skin and a measurement unit according to the present disclosure may be attached to the electrode patch. A person in charge of the measurement session may check the quality of EMG signals, and start a continuous measurement of EMG and motion which may last for several days, for example. During the measurement, the person is free to move and do his/her daily activities. The principal component or components that have been selected for analysis can be used e.g. as a function of time to track changes in patient's condition during the daily activities, for example. For example, FIG. 7 shows an exemplary curve of the first (i.e. the most significant) principal component PC1 of a patient with Parkinson's disease as a function of time. The first principal component PC1 fluctuates over time. The range of fluctuation of PC1 may be considered to represent the range of magnitude of symptoms. The sign of the value of the PC1 depends on the orientation of the basis vector of PC1. In FIG. 7, a large value of PC1 (e.g. a value above the mean of PC1) represents more symptoms while a small value (e.g. a value below the mean of PC1) represents less symptoms. With this kind of curve, medical personnel can easily observe the amount of symptoms in a continuous, long-term format with respect to time instances of providing treatment/medication, for example.

The monitoring system and measurement unit according to the present disclosure may be used together with DBS therapy of PD patients, for example. The analysis results may be used as help for adjusting the DBS settings. By performing the measurement before and after the adjustment of DBS settings, the outcome of DBS setting changes can be evaluated. By performing the measurement before and after DBS surgery, the outcome of DBS surgery can be evaluated.

The monitoring system and measurement unit according to the present disclosure may also be used together with drug therapy of PD patients. Analysis results describing the time-varying symptoms may be used as an aid for adjusting the drug therapy such as for choosing optimal drug types, for adjusting drug dosages, and for scheduling of drug doses. The analysis results may also be used as help in screening the need for other type of therapy such as the need for DBS therapy.

The monitoring system and measurement unit according to the present disclosure may also be used in a clinical trial of drug development. Analysis results may help the drug developers in comparing different drugs and/or evaluating drug efficacy.

The monitoring system and measurement unit according to the present disclosure may also be utilized in real time, e.g. during a surgical operation such as an implantation of neurostimulation system. For example, the monitoring system and measurement unit may be used during implantation of a Deep Brain Stimulator (DBS) electrode. During the implantation, the surgeon may follow at least one time-varying principal component as a graph, for example. The graph may be similar to the graph shown in FIG. 7, for example. A measurement unit according to the present disclosure may be connected to the patient's skin over the muscle of upper or lower limb with electrodes, and the measurement unit may then measure the electrical activity of the muscle (EMG) and possible motion of the limb. The processing unit in the measurement unit then calculates several parameters from a segment of the EMG signal and from the acceleration signal and forms a feature vector based on these parameters. The feature vector is used for updating the correlation matrix, e.g. as shown in Equation (1). The eigenvectors of the updated correlation matrix are calculated, and the feature vector is projected to the subspace spanned by the eigenvectors. The weights of the projection are used as the principal components. The principal components may be sent to a device that is capable to display them as a two-dimensional graph, so that the surgeon can use this graph as help when implanting the DBS electrode.

Next, some referential aspect related to the monitoring system and measurement unit according to the present disclosure are discussed in more detail. As mentioned above, an electrode patch may be used for the measurement of the EMG. The electrode patch may comprise electrodes positioned for measuring the EMG signal from a muscle in upper or lower limb of the person. The positioning of the electrodes may be such that when a monitoring system receives an EMG signal originating from the electrode patch, the monitoring system is able to detect an indicator of PD in a person. The electrode patch may be disposable or reusable. The electrode patch may be made of a sheet of plastic and/or textile into which electrodes have been embedded, for example. Electrode patch may be flexible or rigid. Electrodes may be wet or dry. The measuring area of the electrodes may be circular or other shaped.

The electrodes are preferably arranged to a specific configuration in order to ensure sufficient information content of the EMG signal. Literature widely recommend using a centre-to-centre distance of 2 cm (0.75 inch) between the measurement electrodes in EMG measurements (see e.g. Hermens H J, Freriks B, Merletti R, Stegeman D, Blok J, Rau G, Disselhorst-Klug C, and Flagg G: European recommendations for surface electromyography. Roessingh Research and Development, ISBN 90-75452-15-2, 1999). However, in order to facilitate receiving electromagnetic signals from deeper inside below skin, a distance wider than the recommended 2 cm may be used in the electrode patch. Two measurement electrodes may be positioned parallel to the muscle fibres at a centre-to-centre distance of more than 2 cm to less than 4 cm, for example. A reference electrode may be positioned such that a distance from a centre of the reference electrode to an axis passing through centres of the measurement electrodes is at least the distance between the measurement electrodes. Preferably, the distance between the centres of the measurement electrodes is 2.5-3 cm. Reference electrode is preferably placed on an inactive area with regards to muscles. When this configuration of electrodes is being used together with the monitoring method/system according to the present disclosure, information content of the EMG signal data can be maximized.

FIG. 1 shows an example of an electrode patch that can be used with a monitoring system according to the present disclosure. In FIG. 1, a diagrammatic view of a top side of a self-adhesive electrode patch 10 is shown. The body 14 of the electrode patch may be made of a flexible material, such as plastics of textile or their combination. The electrode patch 10 comprises two measurement electrodes 11a and 11b, and a reference electrode 12 attached or embedded to the body 14 such that surfaces of the electrodes are exposed on the bottom side of the electrode and form a galvanic connection to the skin of person when the patch is applied. In FIG. 1, the measurement electrodes have essentially circular shapes. The sensing area of the electrode can also be rectangular-shaped if this is more suitable for the manufacturing process. The centres of the measurement electrodes 11a and 11b are positioned at a distance $d_1$ from each other. The distance $d_1$ is 3 cm in FIG. 1. The reference electrode 12 is positioned aside of the measurement electrodes (i.e. laterally displaced at a distance $d_2$ from an axis A passing through the centres of the measurement electrodes 11a and 11b). The distance $d_2$ may be at least the distance $d_1$, preferably at least twice the distance $d_1$.

The body 14 of the electrode patch 10 may have a self-adhesive surface on its bottom side and a water resistant coating on its top side. The patch 10 in FIG. 1 may be provided with elongated openings that allow the skin below the patch to breathe. The top side of the patch 10 may have guide markings that help in positioning the patch correctly. The electrode patch may comprise a peel pad on its side in order to facilitate easy removal of the patch once the measurement has been finished.

FIG. 1 also shows a measurement unit 13 on the top side of the electrode patch. The measurement unit 13 is galvanically connected to the electrodes 11a, 11b, and 11c by flexible conducting wires. The measurement unit 13 may be integrated to the electrode patch 10 or it may be detachably connected. For example, the patch may comprise a connector interface in order to form a galvanic connection between the electrodes 11a, 11b, and 12 and a small, wearable measurement unit 14 measuring the EMG of the person. The portable measurement unit 13 may also comprise a motion sensor (such as a acceleration sensor) for providing the motion data used in the method. The measurement unit 13 may be battery-powered and may be detachably attached to the electrode patch 10 via the connector interface 13. The electrode patch may comprise a dock, a pocket or a pouch into which the measurement unit may be placed during use.

The measurement unit 13 in FIG. 1 may be a measurement unit according to the present disclosure. It may further comprise a wireless transceiver unit, and it may be configured to determine a principal component representation of the EMG signal and the motion signal, and transmit the principal component representation to an external system with the wireless transceiver unit. The measurement unit may be configured to perform these steps in real time, or practically in real time.

Figure 2:
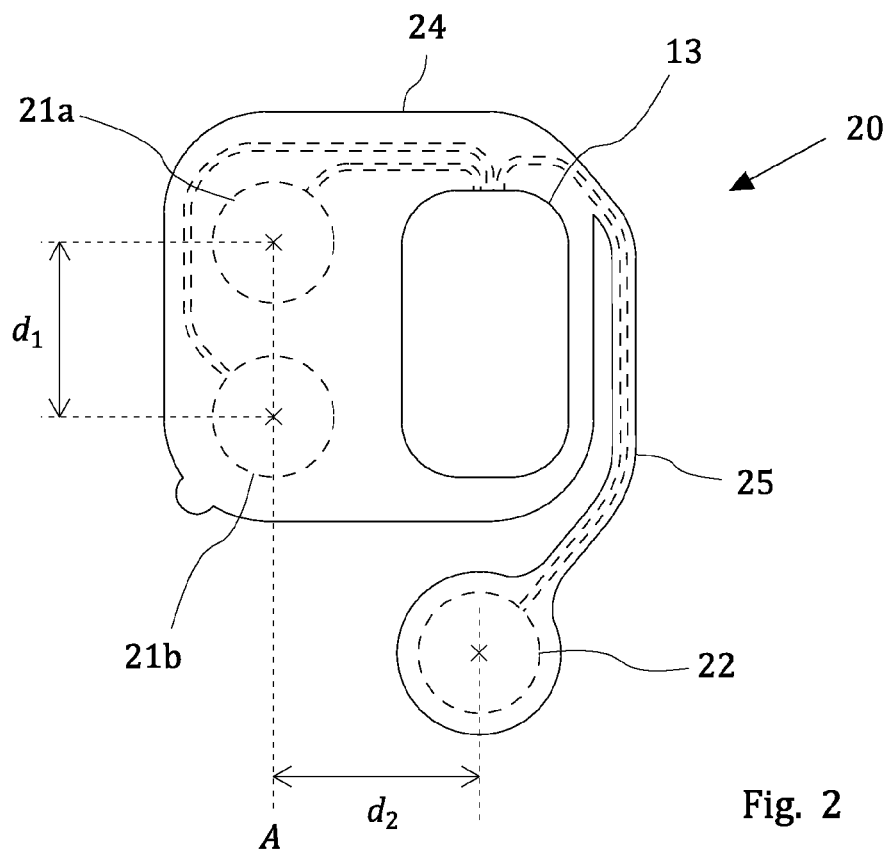
FIG. 2 shows another example of an electrode patch that can be used with a monitoring system according to the present disclosure.

FIG. 2 shows another example of an electrode patch that can be used with a monitoring system according to the present disclosure. The details of the patch 20 are similar in most parts with the patch 10 in FIG. 1. However, a conducting wire forming a connection between the measurement unit 13 and a reference electrode 22 is arranged on the end of a thin, elongated, and flexible strip 25. Said strip 25 extends from the body 24 of the electrode patch 20. This allows adjustment of the position of the reference electrode 22 with respect to the measuring electrodes 21*a* and 21*b* of the electrode patch 20, which may be useful with persons with very large diameter of the limb. The measurement unit 13 may be the same or have the same functionalities as described in the example of FIG. 1.

While the above examples discuss the use of a measurement unit in combination with an electrode patch, the measurement unit and monitoring system according to the present disclosure are not limited only to be used with such an electrode patch. The electrodes can also be in the form of separate electrode at the end of separate leads, for example. However, the electrodes should preferably be positioned based on the principles discussed above. In addition, while wireless communications allow the patient to move more freely during measurements, a measurement unit according to the present disclosure may in some embodiments comprise wired communications means for communicating with the external system.

Further, while the present disclosure mostly discusses implementation of the functionalities of a monitoring system on a measurement unit according to the present disclosure, the monitoring system may alternatively be mostly implemented on an external system. In some implementations, a computer, cluster of computer servers, or a computing cloud acting as the external system may be used to implement the functionalities of a monitoring system according to the present disclosure. A smart phone, tablet computer or other portable computing device capabilities may also be used as the external system implementing the functionalities of a monitoring system according to the present disclosure.

The monitoring system may receive the measurement data directly from a sensor module or the measurement data may be relayed via transceiver unit. The transceiver unit may be a wireless communications unit, such as a wireless internet router, for example. When a computer, cluster of computer servers, or a computing cloud acts as the external system, a smart phone, tablet computer or other portable computing device with wireless communications capabilities may also be used a transceiver unit. The measured data may then be analyzed, and the analysis results are provided to a physician or medical doctor, who is in charge of the person's treatment. The doctor makes the decision on whether or not to use the results as help in doing the diagnosis or adjusting treatment.

Figure 4:
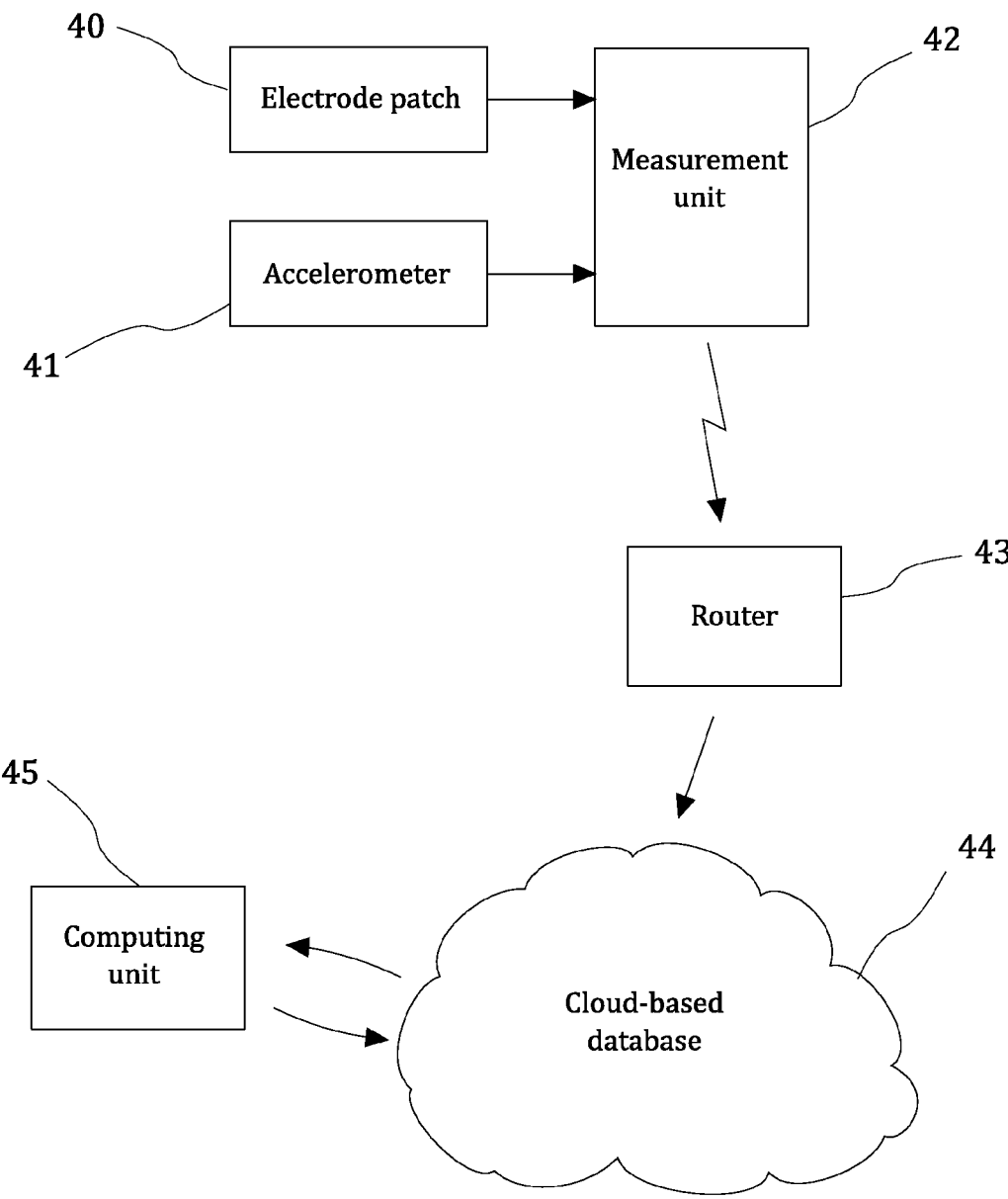
FIG. 4 shows a referential example of a measurement arrangement implementing a monitoring system according to the present disclosure.

FIG. 4 shows an example of a referential measurement arrangement where the calculation of principal components is performed outside the measurement unit. In FIG. 4, electrical activation of a muscle is registered (in the form of an EMG signal) by using an electrode patch 40. The electrode patch 40 may be the same as or similar to the examples of FIGS. 1 and 2, for example. In addition, limb motion is simultaneously registered in FIG. 4 by using an accelerometer 41. In some embodiments, the accelerometer 41 may be integrated to the measurement unit. Alternatively, the accelerometer may be a separate unit.

In FIG. 4, the electrode patch 40 and the accelerometer 41 provide an EMG signal and an acceleration signal (e.g. in the form of analog voltage signals) to a measurement unit 42 where the signals may be A/D converted. Instead of calculating the principal component representation on the measurement unit, the A/D-converted signal data may be either saved into a memory card of the measurement unit 42 (i.e. off-line mode), or sent to a router device 43 (i.e. online mode) that may be a computer or a smart device, for example. In the offline mode, after a measurement session has ended, the measurement data may be uploaded from the memory card to the router device 43. In the online mode, the measurement unit may send some or all signal data to the router device already before the end of a measurement session. Preferably, the communication between the measurement unit 42 and the router 43 is wireless as this allows the person to move more freely. The router device 43 may be a wireless communications unit, such as a wireless internet router, for example. A smart phone, tablet computer or other portable computing device with wireless communications capabilities may also be used as the router device 43.

The signal data provided by the measurement unit 42 to the router device 43 may be a raw A/D-converted signal data or it may be preprocessed by the measurement unit 42. For example, the measurement unit may be configured to perform one or both of steps 32 and 33 in the embodiment of FIG. 3. The measurement unit 42 in FIG. 4 may support both the offline mode and the online mode, and a user may select which of the two modes to use.

In FIG. 4, the signal data is forward to a cloud-based database 44 from the router device 43. From the cloud-based database 44, the signal data is sent to a computing unit 45 that may be a computer or server containing an analysis program, for example. The analysis program may be in the form of a software program. Thus, the analysis program may be configured for monitoring an indicator of PD in the person. The analysis program may be configured to receive (e.g. from the cloud-based database 44) an EMG signal originating from an electrode patch attached to a limb of the person and a motion signal (in the form of an acceleration signal) associated with the EMG signal, determine a principal component representation of the EMG signal and the motion signal, wherein the principal component representation represents a projection of at least one feature of the EMG signal and the motion signal into a feature space formed by orthogonal basis vectors, and determine a value of the indicator of PD based on the principal component representation. For example, the analysis program may implement the steps 34 to 37 of the example of FIG. 3 in order to monitor an indicator of Parkinson's disease.

Once the analysis program in computing unit 45 has been executed, the analysis results may be sent from the computing unit back 45 to the cloud-based database 44, from where they can be accessed by the doctor who is either in charge of the person's treatment or asked to give his/her statement on results, for example It is obvious to a person skilled in the art that the measurement unit and monitoring system can be implemented in various ways. The invention and its embodiments are not limited to the examples described above but may vary within the scope of the claims.

The invention claimed is:

1. A monitoring system comprising:

an electrode patch comprising:

measurement electronics positioned on the electrode patch configured for continuously measuring an electromyography (EMG) signal from only a single limb of a person comprising:

measurement electrodes configured to be positioned parallel to muscle fibers of the limb, and a reference electrode configured to be placed on an inactive muscle area of the limb, a motion sensor configured to be attached to the limb for measuring a motion signal from the limb, a processing unit configured to:

select representative time segments of the EMG signal and the motion signal representing muscle activities measured during static and dynamic contractions;

determine the principal component representation of the EMG signal from the representative time segments of the EMG signal and the motion signal in real time, before transmission, by:

extracting the at least one feature of the EMG signal and extracting the at least one feature of the motion signal;

forming a feature vector on the basis of the at least one extracted feature of the EMG signal and the at least one extracted feature of the motion signal;

forming an initial sample correlation matrix from EMG and motion signals of a population; and updating the initial sample correlation matrix in a time recursive manner by forming a new sample correlation matrix on the basis of values of the extracted features and the initial sample correlation matrix;

wherein the principal component representation represents a projection of at least one feature of the EMG signal and at least one feature of the motion signal into at least one uncorrelated feature in a feature space formed by orthogonal basis vectors; and a transceiver unit configured to transmit the principal component representation to an analysis unit;

the analysis unit configured to receive the principal component representation of the EMG signal and the motion signal as a function of time and determine a value of an indicator of Parkinson's Disease based on the principal component representation;

wherein a range of fluctuation of the principal component representation represents a range of magnitude of the person's symptoms; and wherein a value of the principal component representation above a mean of the principal component representation represents a first number of disease symptoms, and a value of the principal component representation below the mean of the principal component representation represents a second number of disease symptoms lower than the first number of symptoms.

2. The monitoring system according to claim 1, wherein determining the principal component representation further comprises:

solving eigenvectors of the sample correlation matrix and using the solved eigenvectors as the orthogonal basis vectors of the feature space, modeling the feature vector as a weighted sum of the orthogonal basis vectors and solving for weights of the weighted sum, and using at least one of the solved weights as a principal component of the principal component representation.

3. The monitoring system according to claim 1, wherein the motion signal is an acceleration signal and the at least one feature of the EMG signal and the motion signal comprise at least:

a sample kurtosis or a crossing rate variable, a recurrence rate of the EMG signal, and a sample entropy of the acceleration signal.

4. The monitoring system according to claim 1, wherein:

the analysis unit is configured to show the received principle component representations as a visual representation on a display.

5. The monitoring system according to claim 2, wherein the motion signal is an acceleration signal and the at least one feature of the EMG signal and the motion signal comprise at least:

a sample kurtosis or a crossing rate variable, a recurrence rate of the EMG signal, and a sample entropy of the acceleration signal.

6. The monitoring system according to claim 2, wherein:

the analysis unit is configured to show the received principal component representation as a visual representation on a display.

7. The monitoring system according to claim 3, wherein:

the analysis unit is configured to show the received principal component representation as a visual representation on a display.

8. The monitoring system according to claim 5, wherein:

the analysis unit is configured to show the received principal component representation as a visual representation on a display.

* * * * *